US009925537B2

(12) United States Patent
Hoffmann (10) Patent No.: US 9,925,537 B2
(45) Date of Patent: Mar. 27, 2018

(54) MICROFLUIDIC DEVICE AND METHOD FOR ANALYZING A SAMPLE OF BIOLOGICAL MATERIAL (71) Applicant: Robert Bosch GmbH, Stuttgart (DE)

(72) Inventor: Jochen Hoffmann, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 44 days.

(21) Appl. No.: 14/672,316

(22) Filed: Mar. 30, 2015

(65) Prior Publication Data
US 2015/0273470 A1 Oct. 1, 2015

(30) Foreign Application Priority Data

Apr. 1, 2014 (DE) .................... 10 2014 206 140

(51) Int. Cl.
*B01L 3/00* (2006.01)
*G01N 15/00* (2006.01)
*G01N 35/00* (2006.01)

(52) U.S. Cl.
CPC ....... *B01L 3/502753* (2013.01); *B01L 3/5025* (2013.01); *B01L 3/502738* (2013.01); *B01L 2200/0652* (2013.01); *B01L 2200/0668* (2013.01); *B01L 2300/0681* (2013.01); *B01L 2300/0864* (2013.01); *B01L 2300/0874* (2013.01); *B01L 2300/0877* (2013.01); *B01L 2400/0487* (2013.01); *G01N 2015/0065* (2013.01); *G01N 2035/00158* (2013.01)

(58) Field of Classification Search
None
See application file for complete search history.

(56) References Cited

U.S. PATENT DOCUMENTS

| 7,687,239 B2 * | 3/2010 | Goldberg | ................ B82Y 5/00 435/7.2 |
| 2009/0081773 A1 * | 3/2009 | Kaufman | ............. G01N 1/2813 435/309.1 |
| 2009/0311717 A1 | 12/2009 | De Sonneville et al. | |
| 2012/0230886 A1 * | 9/2012 | Henry | ................... B01L 3/5027 422/502 |
| 2013/0217063 A1 * | 8/2013 | Metzger | ................... C12Q 1/04 435/32 |
| 2015/0018226 A1 * | 1/2015 | Hansen | .............. G01N 33/5005 506/9 |

FOREIGN PATENT DOCUMENTS

| WO | 2008/072968 A2 | 6/2008 |
| WO | 2011/091037 A2 | 7/2011 |
| WO | 2013/130875 A1 | 9/2013 |

OTHER PUBLICATIONS

Maxim Kalashnikov et al., "A microfluidic platform for rapid, stress-induced antibiotic susceptibility testing of *Staphylococcus aureus*" Lab on a Chip, The Royal Society of Chemistry, vol. 12—Issue 21, Aug. 9, 2012, pp. 4523-4532, XP002719005, Cambridge, GB.
Shuqi Wang et al., "Simple filter microchip for rapid separation of plasma and viruses from whole blood", International Journal of Nanomedicine, Sep. 1, 2012, pp. 5019-5028, vol. 7, XP055201558.

* cited by examiner

*Primary Examiner* — Robert J Yamasaki
(74) *Attorney, Agent, or Firm* — Maginot, Moore & Beck LLP (57) ABSTRACT

A microfluidic device is configured to analyze a sample of biological material. The microfluidic device includes a fluid guide structure constructed in order to divide a sample introduced into the microfluidic device into a plurality of subquantities. The microfluidic device further includes a plurality of reaction chambers each of which is fluidically connected to the fluid guide structure. Each of the reaction chambers has a filter configured to filter out target cells from the sample, and each of the reaction chambers is constructed to receive a sample subquantity. In each of the reaction chambers, a result of a reaction between a target-cell-specific active substance that is different for each of the reaction chambers and the target cells of the sample subquantity that is taken up is acquirable.

10 Claims, 4 Drawing Sheets

MICROFLUIDIC DEVICE AND METHOD FOR ANALYZING A SAMPLE OF BIOLOGICAL MATERIAL

This application claims priority under 35 U.S.C. § 119 to patent application no. DE 10 2014 206 140.7, filed on Apr. 1, 2014 in Germany, the disclosure of which is incorporated herein by reference in its entirety.

The present disclosure relates to a microfluidic device for analyzing a sample of biological material, in addition to a method for analyzing a sample of biological material, in addition to a device for carrying out the steps of the method, and also to a corresponding computer program.

BACKGROUND

An antibiogram represents, for example, a microbiological test method, in the phentotypic determination variant of which the Kirby-Bauer method with a manual procedure and typical incubation times of, for example, 16 to 20 hours, is known and customary. In this case, a sample under test is placed onto a nutrient medium. At certain positions, antibiotic-impregnated disks are placed into the Petri dish. An antibiotic applied in such a manner is extracted by dissolution and can be taken up by bacteria in the sample. The further it diffuses away from the disk, the lower a concentration becomes. At a defined distance from the disk, a concentration is achieved, in which a microbe, despite a low concentration of the antibiotic, can still grow. This is termed the minimal inhibitory concentration. US 2009/0311717 A1 discloses a microfluidic device.

SUMMARY

Against this background, using the approach presented here, a microfluidic device for analyzing a sample of biological material, a method for analyzing a sample of biological material, in addition a device which uses this method, and also finally a corresponding computer program are presented according to the main claims. Advantageous embodiments result from the respective subclaims and the description hereinafter.

According to embodiments of the disclosure, in particular microfluidic structures or process sequences can be provided for an automatic procedure of a sample analysis which requires a plurality of parallel reactions of target cells of the sample with different active substances, in particular an antibiogram, in an LoC system (LoC=Lab on Chip) or chiplaboratory system. For instance, a microfluidic distributor structure can be provided in particular, which can distribute a sample or sample solution onto various reaction chambers or filter chambers. In the reaction chambers, active substances can be examined for their activity with respect to the target cells. The sample here, in the case of an antibiogram as sample analysis, flows through a bacterial filter, in such a manner that bacteria can be fixed from the sample as target cells, for example onto filter membranes. Thereafter, the filters of the various reaction chambers can be incubated with mixtures of nutrient medium and different antibiotics as active substances. On the basis of growth rates of the bacteria in the various reaction chambers, an activity of different antibiotics on the bacteria from the sample can be determined.

Advantageously, according to embodiments of the disclosure, in particular an automated LoC-based method can be provided, by means of which an activity of active substances, for example antibiotics, can be determined individually, reliably and rapidly. In addition to such a speed advantage, wherein a sample analysis can be performed, for example within one hour, embodiments of the disclosure can also be used flexibly, in order to study a variety of possible target cells, wherein, in particular, a usage in the case of MRSA (methicillin-resistant *Staphylococcus aureus*), sepsis or the like is possible. Thus, embodiments of the disclosure have a local advantage to the extent that an increased activity of a treatment or more rapid therapy success can be made possible. Also, embodiments of the disclosure have a global advantage of a reduction of multiple resistant target cells strains, e.g. bacterial strains. Thus, for example, it is possible to prevent, without a previous activity test, new antibiotic resistances from forming, due to increased usage of broad-spectrum antibiotics, wherein a single genetic determination pursues mutating strains. An antibiogram can even deliver diagnostically important information for choice of an effective antibiotic here. On the basis of analytical results according to embodiments of the disclosure, an identity of target cells or of a strain of a bacterium can be concluded indirectly, or without genetic profiling, for example if it was determined in the analysis that target cells or a bacterial colony is resistant to certain antibiotics as active substances. Therefore, genetic profiling can advantageously be dispensed with, as a result of which a multiplicity of complex LoC unit operations such as, for example, lysis, purification, amplification, microarray detection and the like, can be saved.

A microfluidic device for analyzing a sample of biological material is presented, wherein the microfluidic device has the following features:

fluidic guide means which are constructed to divide a sample introduced into the microfluidic device into a plurality of subquantities; and a plurality of reaction chambers which are fluidically connected to the fluid guide means, wherein each of the reaction chambers has a filter for filtering out target cells from the sample, wherein each of the reaction chambers is constructed to take up a sample subquantity, wherein, in each of the reaction chambers, a result of a reaction between a target-cell-specific active substance that is different for each of the reaction chambers and the target cells of the sample subquantity that is taken up is acquirable.

The microfluidic device can be used, for example, in combination with analytical systems, in particular for microfluidic Lab-on-Chip systems for environmental analysis or medical diagnosis. The microfluidic device can be a microfluidic system or an analytical device, in particular a microfluidic Lab-on-Chip or chiplaboratory for medical diagnosis, microbiological diagnosis or environmental analysis. The sample can be a liquid that is to be analyzed, typically a liquid or liquefied patient sample, e.g. blood, urine, feces, sputum, cerebrospinal fluid, lavage, a rinsed smear or a liquefied tissue sample, or a sample of a non-human material. Target cells present in the sample can comprise, for example, pathogenic cells or pathogens, e.g. microorganisms, such as, e.g. bacteria or fungi, human cells, e.g. blood cells or the like, or animal cells. The fluid guide means can comprise fluid channels or fluid guide lines, valves and/or at least one transport appliance. In each reaction chamber, a reaction can be carried out between a target-cell-specific active substance and the target cells of the sample subquantity that is taken up in the respective reaction chamber. The reaction can be, in particular, an antibiogram or the like. The active substances can differ with respect to their type, identity and/or concentration. As active substances, for example antibiotics, antimycotics or the like can be used.

The microfluidic device can also be constructed in order to carry out or permit a lysis, in particular a selective lysis, of the sample, or to facilitate or permit the target cells to be filtered out.

According to one embodiment, in each of the reaction chambers, a different active substance can be introducible or introduced. In this case, the active substance can be combined with a support material, wherein a separation of the active substance from the support material is made possible in the reaction chambers. The support material in this case can be in a solid state or present as a high-viscosity liquid. Such an embodiment offers the advantage that analysis of the sample can be further simplified and accellerated since the active substances are already precharged in the reaction chambers and only the subquantities of the sample need to be distributed onto the reaction chambers.

Alternatively, or in addition thereto, the microfluidic device can have a plurality of storage chambers for the storage of different active substances. In this case, the storage chambers can be fluidically connected by means of the fluid guide means to the plurality of reaction chambers. In this case the fluid guide means can be constructed to introduce one of the different active substances from the storage chambers into each of the reaction chambers. In this case, in each of the storage chambers, a different active substance can be introduced or introducible. The active substances can be stored in the storage chambers in liquid form or in a liquid support material. Also, further substances can be storable in the storage chambers and introducible into the reaction chambers. Such an embodiment offers the advantage that the active substances can be introduced in a simple manner and/or according to demand in a flexible manner adaptable to the reaction chambers.

Also, in this case, the fluid guide means can have a plurality of collecting channels and a plurality of feed valves. Here, each of the storage chambers can be fluidically connected by means of a collecting channel to the plurality of reaction chambers, wherein a feed valve can be arranged in each collecting channel. Such an embodiment offers the advantage that a reliable storage and removal of active substances can be made possible without mixing the same.

In addition, the fluid guide means can have a sample intake channel having an intake valve, a pump chamber, a plurality of distribution channels having a plurality of first pump valves, a plurality of discharge channels having a plurality of second pump valves, and a waste chamber. In this case, the sample intake channel can be fluidically connected to the pump chamber. Also, the pump chamber and the reaction chambers can be fluidically connected to one another by means of the plurality of distribution channels. In addition, the reaction chambers and the waste chamber can be fluidically connected to one another by means of the plurality of discharge channels. Such an embodiment offers the advantage that simple and reliable division of the sample and also disposal of a target-cell-free sample fraction can be made possible.

In addition, each of the reaction chambers can be constructed or designed in order to make the result of the reaction between the active substance and the target cells of the sample subquantity that is taken up optically and/or electrically acquirable. In this case, each of the reaction chambers can have at least one optically permeable section. In addition, a vital-staining dye can be prechargeable or introducible into the reaction chambers. Also, each of the reaction chambers can have electrodes for impedance measurement mounted on the filter. Acquisition means for acquiring the result of the reaction can be assigned to the plurality of reaction chambers. Such an embodiment offers the advantage that the sample can be analyzed or evaluated in a simple, rapid and reliable manner.

A method is also presented for analyzing a sample of biological material, wherein the method can be carried out in combination with a microfluidic device which has fluid guide means and a plurality of reaction chambers that are fluidically connected to the fluid guide means and have filters, wherein the method has the following steps:

dividing a sample introduced into the microfluidic device into a plurality of subquantities by means of the fluid guide means onto the plurality of reaction chambers, wherein each of the subquantities of the sample is distributed onto one of the reaction chambers;

filtering out target cells from the sample by means of the filters of the reaction chambers; and carrying out a reaction between a target-cell-specific active substance that is different for each of the reaction chambers and the target cells of the sample in each of the reaction chambers, in order to make a result of the reaction between the active substance and the target cells of the sample acquirable in each of the reaction chambers.

The method can be advantageously carried out in combination with an embodiment of the abovementioned microfluidic device in order to analyze a sample of biological material. The step of division, the step of filtering out, and in addition or alternatively, the step of the procedure, can be carried out by actuating fluid guide means, for example at least one valve, and in addition, or alternatively, at least one transport appliance. In this case, fluid guide means, for example the valves, and in addition, or alternatively, the at least one transport appliance, can have interfaces which are constructed to receive actuation signals. In the step of division, and in the step of filtering out, the sample can be transported by means of the fluid guide means within the microfluidic device. In the step of the procedure, according to one embodiment, the active substances can be transported by means of the fluid guide means into the reaction chambers. Also, the method, upstream of the step of filtering out, can have a step of lysis of the samples, wherein the target cells remain intact.

The approach presented here further provides a device which is constructed in order to carry out, actuate or implement the steps of a variant of a method presented here in corresponding appliances. Also, the problem underlying the disclosure can be solved rapidly and efficiently by this embodiment variant of the disclosure in the form of a device.

A device in the present case can be taken to mean an electrical apparatus which processes sensor signals and, in dependence thereon, outputs control and/or data signals. The device can have an interface which can be constructed in terms of hardware and/or software. In the case of a construction in terms of hardware, the interfaces can be, for example, part of what is termed a system-ASIC, which comprises the most varied functions of the device. However, it is also possible that the interfaces are independent integrated circuits, or at least in part consist of discrete components. In the case of a construction in terms of software, the interfaces can be software modules which are present, for example, on a microcontroller in addition to other software modules.

A computer program product which can be stored on a machine-readable support such as a semiconductor store, a hard drive store or an optical store and is used for carrying out and/or actuating the steps of the method according to one of the above-described embodiments is also advantageous, in particular when the program product is carried out on a computer or a device.

BRIEF DESCRIPTION OF THE DRAWINGS

The approach presented here will be explained in more detail hereinafter by way of example with reference to the accompanying drawings, in which.

DETAILED DESCRIPTION

In the description hereinafter of favorable exemplary embodiments of the present disclosure, for the elements shown in the various figures and acting in a similar manner, identical or similar reference signs are used, wherein a repeated description of these elements is avoided.

Figure 1:
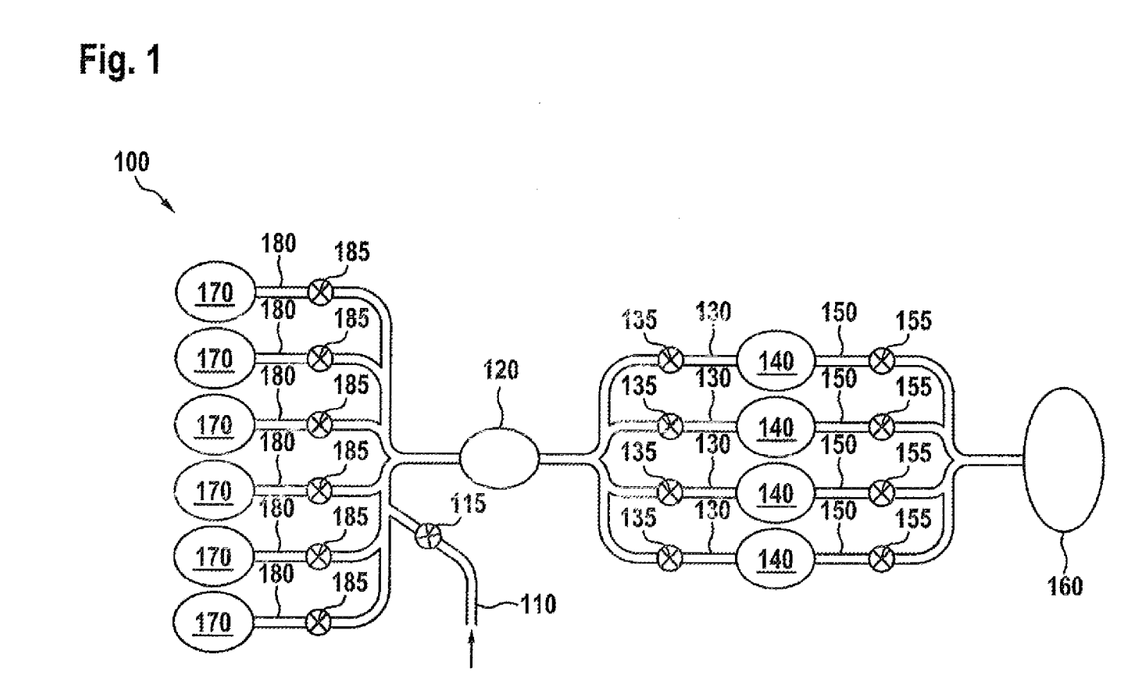
FIG. 1 shows a schematic drawing of a microfluidic device according to an exemplary embodiment of the present disclosure.

FIG. 1 shows a schematic drawing of a microfluidic device 100 for analyzing a sample of biological material according to an exemplary embodiment of the present disclosure. The microfluidic device 100 in this case is constructed as a microfluidic Lab-on-Chip (LoC) or chip-laboratory for medical diagnosis, microbiological diagnosis or environmental analysis. In particular, the microfluidic device 100 is constructed for analyzing the sample to prepare an antibiogram with respect to target cells of the sample and different active substances. What is shown of the microfluidic device 100 in this case are a sample intake channel 110, an intake valve 115, a pump chamber 120, a plurality of distribution channels 130, a plurality of first pump valves 135, a plurality of reaction chambers 140, a plurality of discharge channels 150, a plurality of second pump valves 155, a waste chamber 160, a plurality of storage chambers 170, a plurality of collection channels 180 and a plurality of feed valves 185.

The sample intake channel 110, the intake valve 115, the pump chamber 120, the plurality of distribution channels 130, the plurality of first pump valves 135, the plurality of discharge channels 150, the plurality of second pump valves 155, the plurality of collecting channels 180, and the plurality of feed valves 185 represent here fluid guide means of the microfluidic device 100. The fluid guide means are constructed to divide a sample introduced into the microfluidic device 100 into a plurality of subquantities. Also, the fluid guide means are constructed in order to transport the sample and also active substances within the microfluidic device 100.

Via the sample intake channel 110, a target-cell containing sample of biological material is introducible into the microfluidic device 100. The intake valve 115 is arranged in the sample intake channel 110. The intake valve 115 is constructed to switchably clear or block the sample intake channel 110. The sample intake channel 110 is fluidically connected to the pump chamber 120. In accordance with the exemplary embodiment of the present disclosure shown in FIG. 1, the sample intake channel 110 opens out adjacent to the pump chamber 120 into one of the collecting channels 180.

The plurality of storage chambers 170 are constructed for storing different active substances. In each storage chamber 170, a different active substance is storable. The storage chambers 170 are fluidically connected to the pump chamber 120 by means of the plurality of collecting channels 180. In this case, each of the storage chambers 170 is fluidically connected to the pump chamber 120 by means of a collecting channel 180. In each collecting channel 180, in this case, a feed valve 185 is arranged. The feed valves 185 are constructed to switchably individually clear or block the collecting channels 180.

The pump chamber 120 represents a transport appliance of the fluid guide means of the microfluidic device 100. In this case the collecting channels 180 and the sample intake channel 110 open out into the pump chamber 120. In accordance with the exemplary embodiment of the present disclosure shown in FIG. 1, in this case the collecting channels 180 and the sample intake channel 110 combine adjacently to the pump chamber 120. The distribution channels 130 exit from the pump chamber 120. Thus, the pump chamber 120 is fluidically connected between the collecting channels 180 and the sample intake channel 110 on the one hand, and the distribution channels 130 on the other hand. The distribution channels 130 exit in a shared channel section from the pump chamber 120 and branch off adjacently to the pump chamber 120 into the plurality of distribution channels 130. One of the plurality of first pump valves 135 is arranged in each of the distribution channels 130. The first pump valves 135 are constructed to switchably individually clear or block the distribution channels 130.

Figure 3:
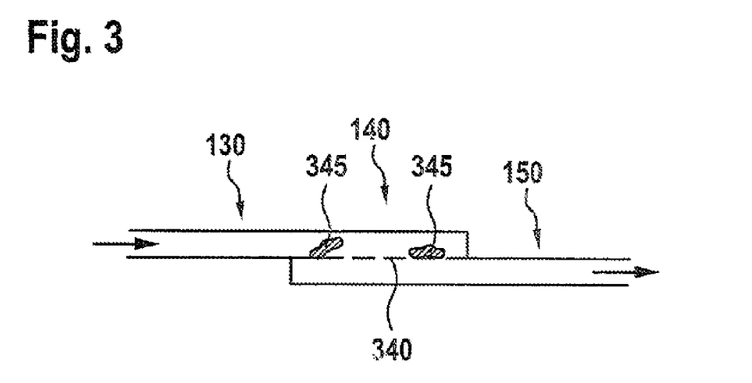
FIG. 3 shows a schematic sectional drawing of a part of a microfluidic device according to an exemplary embodiment of the present disclosure.

The plurality of reaction chambers 140 are fluidically connected to the pump chamber 120 by means of the plurality of distribution channels 130. In this case, each reaction chamber 140 is fluidically connected to the pump chamber 120 by means of a distribution channel 130. Each of the reaction chambers 140 is constructed to take up a sample subquantity. Even if, for reasons of space, it is not shown in FIG. 1, but is shown in FIG. 3, each of the reaction chambers 140 has a filter for filtering out target cells from the sample subquantity that is taken up. Each of the reaction chambers 140 is thus constructed to filter out the target cells from the sample subquantity by means of the filter when a sample subquantity flows through the reaction chamber 140. In this case the plurality of reaction chambers 140 are fluidically connected between the plurality of distribution channels 130 and the plurality of discharge channels 150.

By means of the plurality of discharge channels 150, the plurality of reaction chambers 140 and the waste chamber 160 are fluidically connected to one another. In this case, each reaction chamber 140 is fluidically connected to the waste chamber 160 by means of a discharge channel 150. One of the plurality of second pump valves 155 is arranged in each discharge channel 150. The second pump valves 155 are constructed to switchably individually clear or block the discharge channels 150. The waste chamber 160 is constructed to take up from the reaction chambers 140 substantially target-cell-free sample fractions from which the target cells have been filtered out.

Therefore, in other words, the storage chambers 170 are fluidically connected to the reaction chambers 140 by means of the fluid guide means, here the collecting channels 180, the pump chamber 120 and the distribution channels 130. In this case, the fluid guide means are constructed to introduce into each of the reaction chambers 140 one of the different active substances from one of the storage chambers 170. In each reaction chamber 140 a reaction can be carried out between a target-cell-specific active substance that is different for each of the reaction chambers 140 and the target cells that have been filtered out from the sample subquantity that is taken up into the respective reaction chamber 140.

Also, in each of the reaction chambers 140, a result of the reaction between the active substance and the target cells of the sample subquantity that is taken up into the respective reaction chamber 140 is acquirable. In accordance with an exemplary embodiment, each of the reaction chambers 140 is constructed in order to make the result of the reaction between the active substance and the target cells of the sample subquantity that is taken up optically and additionally or alternatively electrically acquirable. In this case, each of the reaction chambers 140 can have at least one optically permeable section, a vital-staining dye can be prechargeable or introducible into the reaction chambers 140, or each of the reaction chambers 140 can have electrodes mounted on the filter for impedance measurement. Also, the microfluidic device 100 for this purpose can have acquisition means for acquiring the result of the reaction assigned to the plurality of reaction chambers 140.

In other words, FIG. 1 shows a plan view of an exemplary embodiment of a microfluidic device 100 or of a microfluidic chip, wherein, as active substances in the storage chambers 170, antibiotics are prechargeable or are precharged in the liquid state or in a liquid form. The microfluidic device 100 comprises the pump chamber 120 and also the intake valve 115, the plurality of first pump valves 135 and the plurality of second pump valves 155 which are constructed to distribute a bacteria-containing sample over the sample intake channel 110 or an inlet to the reaction chambers 140 or filter chambers. In a first process step, a preprocessed sample solution is flushed through the reaction chambers 140. Pores of the filters in the reaction chambers 140 are dimensioned in accordance with the exemplary embodiment shown in FIG. 1 in such a manner that bacteria are filtered out. The sample can be preprocessed, for example, using a suitable appliance in order to lyse or disrupt human cells selectively in comparison with bacteria. The remaining sample surplus is passed into the waste chamber 160. Subsequently, the reaction chambers 140 can be washed in order to remove residues of human cells. In a subsequent step, each of the reaction chambers 140 is flooded with a mixture of a bacterial nutrient medium which, for example, can be fed via the sample intake channel 110, and an antibiotic as active substance from one of the storage chambers 170, and kept in the reaction chambers 140 by closing the pump valves 135 and 155. An activity of the antibiotics on an organism is acquirable on the basis of a growth rate of the bacteria on the filters in the reaction chambers 140 in real time or by end-point measurement.

Figure 2:
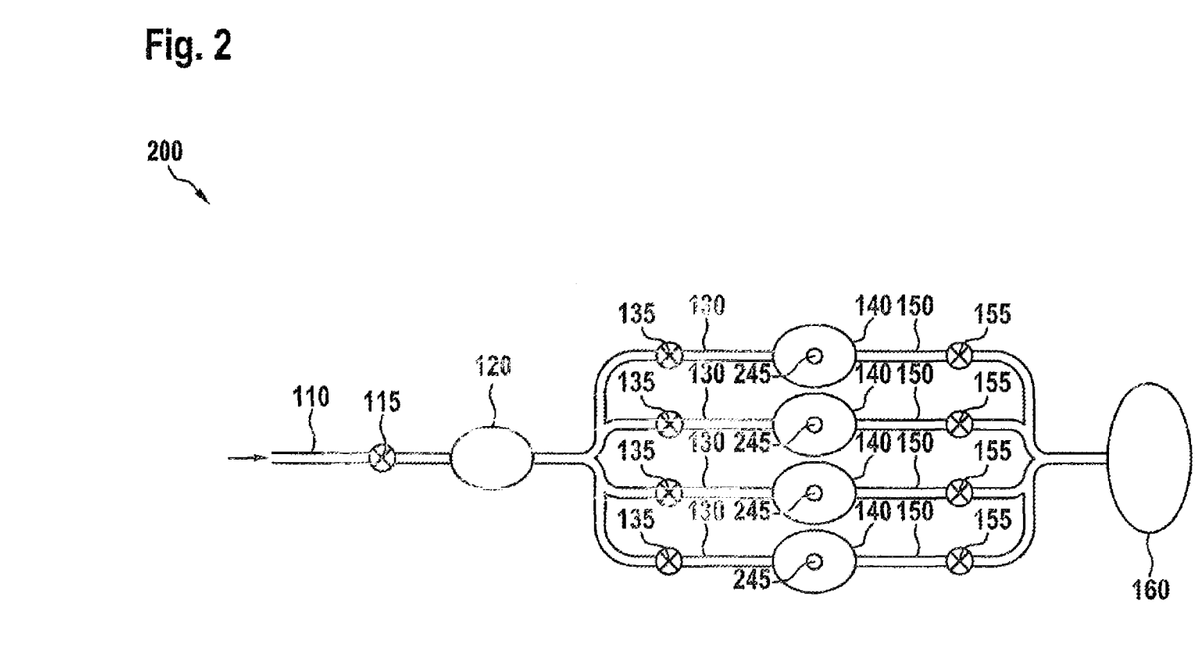
FIG. 2 shows a schematic drawing of a microfluidic device according to an exemplary embodiment of the present disclosure.

FIG. 2 shows a schematic drawing of a microfluidic device 200 in accordance with an exemplary embodiment of the present disclosure. In this case the microfluidic device 200 corresponds to the microfluidic device from FIG. 1, with the exception that the microfluidic device 200 according to the exemplary embodiment shown in FIG. 2 does not have storage chambers and active substances 245 are precharged in solid form in the reaction chambers 140. Thus, in FIG. 2 of the microfluidic device 200, there are shown the sample intake channel 110, the intake valve 115, the pump chamber 120, the plurality of distribution channels 130, the plurality of first pump valves 135, the plurality of reaction chambers 140, the plurality of discharge channels 150, the plurality of second pump valves 155, the waste chamber 160 and the active substances 245. The sample intake channel 110 in this case opens out directly into the pump chamber 120. In each of the reaction chambers 140, a different active substance 245 is precharged.

In other words, FIG. 2 shows a plan view of an exemplary embodiment of a microfluidic device 200 or of a microfluidic chip, wherein, as active substances 245, antibiotics are precharged in solid form in the reaction chambers 140. The microfluidic device 100 comprises the pump chamber 120 and also the intake valve 115, the plurality of first pump valves 135 and the plurality of second pump valves 155 which are constructed to distribute a bacteria-containing sample over the sample intake channel 110 or an inlet onto the reaction chambers 140 or filter chambers. Each reaction chamber 140 contains a matrix, for example a filter or a filter disk with an antibiotic in solid form. In a first process step, a preprocessed sample solution is flushed through the reaction chambers 140. The sample can be preprocessed, for example using a suitable appliance, in order to lyse or disrupt human cells selectively in comparison with bacteria. Pores of the filter in the reaction chambers 140 are dimensioned in accordance with the exemplary embodiment shown in FIG. 1 in such a manner that bacteria are filtered out. The remaining sample surplus is passed into the waste chamber 160. After a flushing of the reaction chambers 140 in order to remove cell residues of human cells, in a next step each of the reaction chambers 140 is filled with a bacterial growth medium which can be fed, for example, via the sample intake channel 110. The antibiotics, for example, precharged in disks, are taken up by the bacterial growth medium. The reaction chambers 140 that are closed by the pump valves 135 and 155 then contain the bacteria fixed on the filters and the growth medium having a dissolved antibiotic. An activity of the antibiotics on an organism is measurable in real time or by end-point on the basis of a growth rate of the bacteria on the filters in the reaction chambers 140.

FIG. 3 shows a schematic sectional view of a part of a microfluidic device according to an exemplary embodiment of the present disclosure. The part of the microfluidic device is, for example, a part of the microfluidic device 100 of FIG. 1, or of the microfluidic device 200 of FIG. 2. In this case, a part of a distribution channel 130, a reaction chamber 140, a part of a discharge channel 150, a filter 340 arranged in the reaction chamber 140 and also filtered-out target cells 345, which are, in this case, for example bacteria, are shown. The filter 340 is constructed to be impermeable to the target cells 340. The reaction chamber 140 is subdivided by the filter 340 into a section on the vertical channel side and a section on the discharge channel side. The target cells 345 that are filtered out are arranged in the section on the vertical channel side lying on the filter 340.

Figure 4:
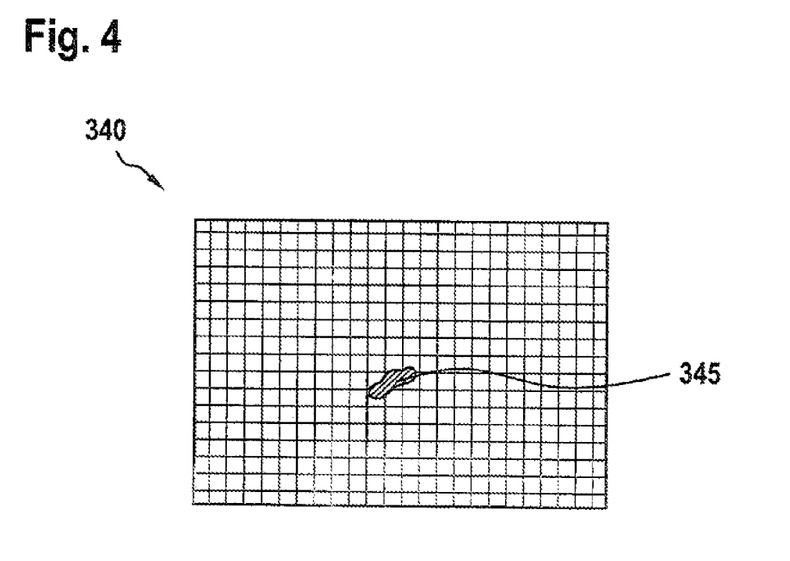
FIGS. 4 and 5 show drawings of filters of a microfluidic device according to exemplary embodiments of the present disclosure.

FIG. 4 shows a drawing of a filter 340 of a microfluidic device according to an exemplary embodiment of the present disclosure. The microfluidic device is, for example, the microfluidic device 100 of FIG. 1, or the microfluidic device 200 of FIG. 2. The filter 340 is, for example, the filter of FIG. 3. In other words, FIG. 4 shows a plan view of a reaction chamber or filter chamber having the filter 340. A target cell 345 that is filtered out is arranged by way of example on the filter 340. In FIG. 4, in this case, a bacterium is shown schematically as the target cell 345 on the filter 340, for example before incubation with an antibiotic as active substance.

Figure 5:
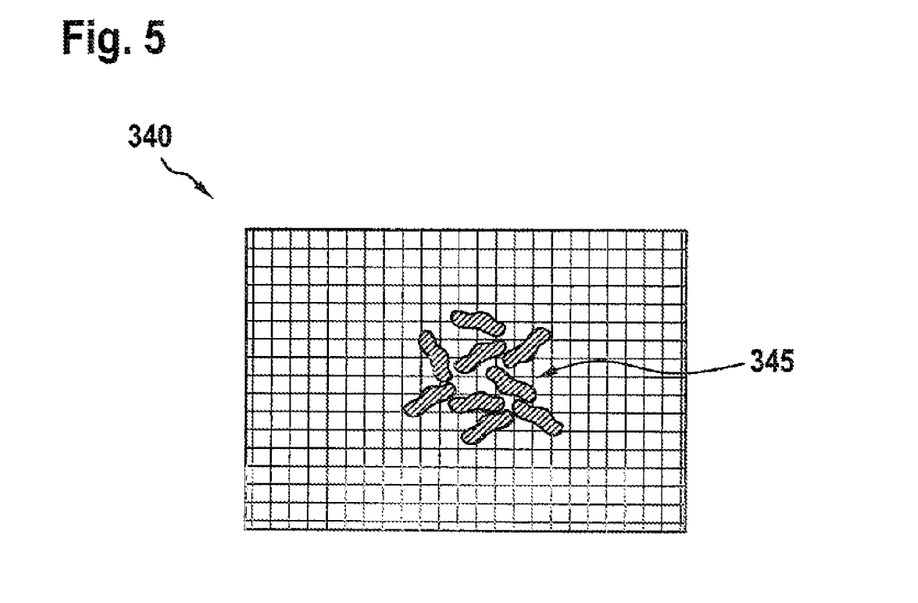

FIG. 5 shows a drawing of a filter 340 of a microfluidic device according to an exemplary embodiment of the present disclosure. The microfluidic device is, for example, the microfluidic device 100 of FIG. 1, or the microfluidic device 200 of FIG. 2. The filter 340 is, for example, the filter of FIG. 3. The drawing of FIG. 5 corresponds to the drawing of FIG. 4 with the exception that on the filter 340, in this case in FIG. 5, a plurality of target cells 345 are arranged. A state shown in FIG. 5 in a reaction chamber with the plurality of target cells 345 on the filter 340 corresponds, for example, to an acquirable result of a reaction in the reaction chamber. In other words, the plurality of target cells 345 represents a bacterial culture which is, for example, resistant to a certain antibiotic which was used as active substance in the reaction chamber.

Figure 6:
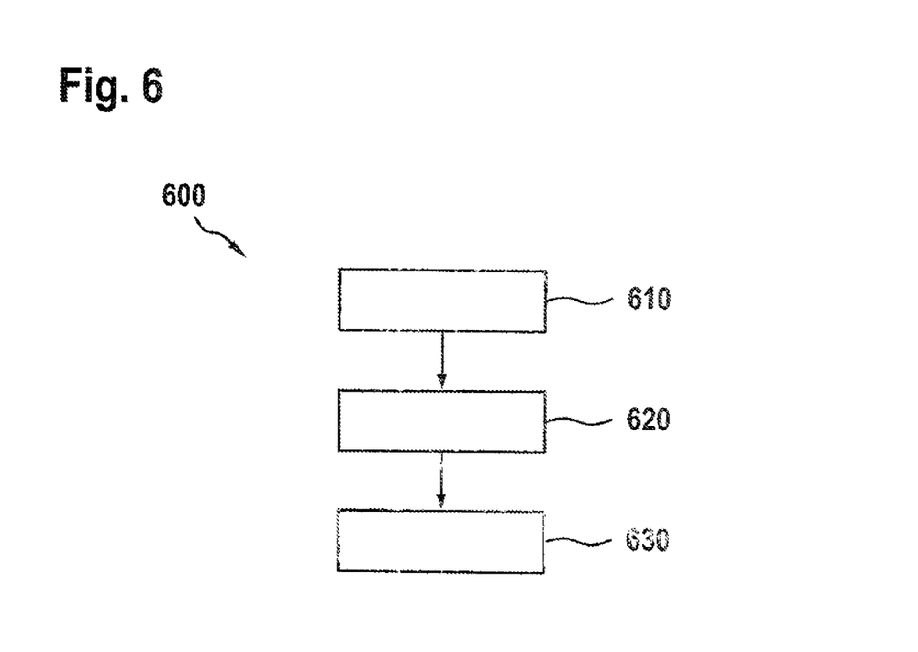
FIG. 6 shows a sequence diagram of a method according to an exemplary embodiment of the present disclosure.

FIG. 6 shows a sequence diagram of a method 600 for analyzing a sample of biological material according to an exemplary embodiment of the present disclosure. In this case the method 600 can be carried out in combination with a microfluidic device which has fluid guide means and a plurality of reaction chambers that are fluidically connected to the fluid guide means and have filters. In other words, the method 600 can be carried out in combination with a microfluidic device such as the microfluidic device of FIG. 1 or FIG. 2. In particular, the method 600 can be carried out in order to analyze the sample to prepare an antibiogram with respect to target cells of the sample and different active substances.

The method 600 has a step 610 of dividing a sample introduced into the microfluidic device into a plurality of subquantities by means of the fluid guide means onto the plurality of reaction chambers. In this case, each of the sample subquantities is distributed onto one of the reaction chambers. Also, the method 600 has a step 620 of filtering out target cells from the sample by means of the filters of the reaction chambers. In addition, the method 600 has a step 630 of carrying out a reaction between a target-cell-specific active substance that is different for each of the reaction chambers, and the target cells of the sample in each of the reaction chambers, in order to make a result of the reaction between the active substance and the target cells of the sample acquirable in each of the reaction chambers.

Optionally, the method 600, before the step 620 of filtering out, can have a step of disruption or lysis of the sample, in such a manner that the target cells remain intact. According to an exemplary embodiment, the step 610 of division, the step 620 of filtering out, and in addition, or alternatively, the step 630 of carrying out by actuating fluid guide means are carried out. In this case, fluid guide means have interfaces which are constructed to receive actuating signals. In step 610 of division, and in step 620 of filtering out, in this case, the sample is transported within the microfluidic device by means of the fluid guide means. In step 630 of carrying out, in this case the active substances are transported into the reaction chambers by means of the fluid guide means.

Hereinafter, characteristics of exemplary embodiments of the present disclosure are summarized and explained in other words with reference to FIGS. 1 to 6.

An antibiogram is the name for a laboratory test for determining a sensitivity or resistance of pathogens, which in this case represent the target cells, to antibiotics as active substances. In principle, an antibiogram is advisable before administration of an antibiotic. In the context of a phenotypic determination, for example a growth rate of bacteria is measured in the presence of a nutrient medium and certain antibiotics. This approach is in contrast to in-vitro methods for preparing genetic profiles of bacteria, also called genotypic determination. The latter methods can suffer from the fact that only a few genetic profiles or features of antibiotic-resistant bacteria are known. Examples of a known antibiotic resistance are, inter alia, the mecA gene or the nptII gene. By increased usage of broad-band antibiotics without prior activity testing, new antibiotic resistances constantly form, for which reason a sole genotypic determination is not future-proofed. A phenotypic determination, as is permitted using exemplary embodiments of the present disclosure, can provide a remedy here.

Exemplary dimensions of microfluidic devices 100 or 200 according to exemplary embodiments of the present disclosure comprise, for example, a thickness of the microfluidic device 100 or 200 of 0.5 millimeters to 5 millimeters, a diameter of the channels 110, 130, 150 and 180 of 10 micrometers to 3 millimeters, a volume of the chambers 120, 140, 160 and 170 of 1 cubic millimeter to 1000 cubic millimeters, a pore size of the filters 340 of 0.05 micrometers to 50 micrometers, and a number of precharged active substances 245 or antibiotics of 1 to 100. In this case, precharging the antibiotics can proceed as active substances 245 in liquid or solid form, for example in the form of filter disks impregnated with antibiotics and dried. Filtering out 620 accompanying cells or target-cell-free sample fractions, or fixing exclusively target cells, here, for example, exclusively bacteria, on the filter 340, proceeds in particular by previous filtering out of accompanying cells, for example human cells, by an upstream filter, or by removing accompanying cells by selective lysis. Filters 340 which can be used are what are termed transmission electron microscope grids, or TEM grids, what are termed track-etched filters, lithographically produced filters, HEPA bacterial filters, membrane filters, cloth filters or the like. Acquisition or measurement of a bacterial growth can proceed by means of optical monitoring, for example by means of a microscope, by means of impedance measurement via electrodes mounted on the filter 340, using vital-staining dyes, for example, almarBlue, PrestoBlue, LIVE/DEAD BacLight, Microbial Viability Assay Kit-WST, etc., or the like.

The exemplary embodiments described and shown in the figures are only selected by way of example. Different exemplary embodiments can be combined with one another completely or in respect of individual features. Also, an exemplary embodiment can be supplemented by features of a further exemplary embodiment.

In addition, the method steps presented here can be repeated and also carried out in a sequence other than that described.

If an exemplary embodiment comprises an "and/or" link between a first feature and a second feature, this is to be read that the exemplary embodiment, according to one embodiment, has not only the first feature but also the second feature, and according to a further embodiment, has either only the first feature or only the second feature.

What is claimed is:

1. A method for analyzing a sample of biological material, wherein the method is carried out in combination with a microfluidic device, the microfluidic device including a fluid guide structure and a plurality of reaction chambers that are each fluidically connected to the fluid guide structure and have filters, the method comprising:

dividing a sample introduced into the microfluidic device into a plurality of subquantities with the fluid guide structure, each of the subquantities of the sample distributed into one of the reaction chambers;

filtering out target cells from the sample with the filters of the reaction chambers;

carrying out a reaction in each of the reaction chambers between a target-cell-specific active substance that is different for each of the reaction chambers and the filtered target cells of the sample; and acquiring a result of the reaction while the filtered target cells of the sample remain in each of the reaction chambers, wherein acquiring a result of the reaction comprises measuring impedance via electrodes mounted on the filters of each of the reaction chambers.

2. The method according to claim 1, wherein a device is configured to carry out the method.

3. The method according to claim 1, wherein a computer program is equipped to carry out the method.

4. The method according to claim 3, wherein the computer program is stored on a machine-readable storage medium.

5. The method according to claim 1, wherein filtering out target cells from the sample comprises:

flushing each of the subquantities of the sample through the filters of the reaction chambers, and capturing at least one target cell in pores of the filters of the reaction chambers.

6. The method according to claim 1, wherein carrying out the reaction in each of the reaction chambers between the active substance and the target cells includes:

flooding each of the reaction chambers with the active substance, and retaining at least a portion of the active substance in each of the reaction chambers.

7. The method according to claim 6, wherein flooding each of the reaction chambers with the active substance comprises:

storing the active substance in a storage chamber, the different active substances for each of the reaction chambers stored in different storage chambers, opening a first pump valve and a second pump valve leading into and out of, respectively, each of the reaction chambers, and pumping the active substances from the storage chambers into the reaction chambers.

8. The method according to claim 7, wherein retaining at least a portion of the active substance in each of the reaction chambers comprises:

closing the first and second pump valves.

9. The method according to claim 1, wherein acquiring a result of the reaction comprises:

introducing a vital-staining dye into each of the reaction chambers, and visually perceiving the result of the reaction through at least one optically permeable section of each of the reaction chambers.

10. The method according to claim 1, wherein acquiring a result of the reaction further comprises:

detecting an activity of the active substance on the filtered target cells by measuring growth rates of the filtered target cells on the filters in each of the reaction chambers in real time or by end point, the activity detected by an acquisition mechanism assigned to the plurality of chambers.

* * * * *